United States Patent
Nebosis et al.

(10) Patent No.: US 10,993,686 B2
(45) Date of Patent: May 4, 2021

(54) PHASE CONTRAST IMAGING METHOD

(71) Applicant: AGFA NV, Mortsel (BE)

(72) Inventors: Rainer Nebosis, Munich (DE); Paul Leblans, Munich (DE)

(73) Assignee: AGFA NV, Mortsel (BE)

( * ) Notice: Subject to any disclaimer, the term of this patent is extended or adjusted under 35 U.S.C. 154(b) by 0 days.

(21) Appl. No.: 16/629,979

(22) PCT Filed: Jul. 2, 2018

(86) PCT No.: PCT/EP2018/067786
§ 371 (c)(1),
(2) Date: Jan. 10, 2020

(87) PCT Pub. No.: WO2019/011692
PCT Pub. Date: Jan. 17, 2019

(65) Prior Publication Data
US 2020/0129135 A1    Apr. 30, 2020

(30) Foreign Application Priority Data

Jul. 13, 2017 (EP) .................................... 17181154

(51) Int. Cl.
*A61B 6/00* (2006.01)
*G06T 11/00* (2006.01)
*H04N 5/32* (2006.01)

(52) U.S. Cl.
CPC ............ *A61B 6/484* (2013.01); *A61B 6/4035* (2013.01); *A61B 6/4291* (2013.01); *G06T 11/00* (2013.01); *H04N 5/32* (2013.01)

(58) Field of Classification Search
CPC ............................. A61B 6/484; A61B 6/4035
See application file for complete search history.

(56) References Cited

U.S. PATENT DOCUMENTS

| | | | |
|---|---|---|---|
| 2015/0146861 A1* | 5/2015 | Kobayashi | G01N 23/207 378/79 |
| 2016/0146744 A1 | 5/2016 | Endrezzi et al. | |
| 2018/0188190 A1* | 7/2018 | Durko | G01N 23/20075 |

FOREIGN PATENT DOCUMENTS

| | | |
|---|---|---|
| WO | 2004/102958 A1 | 11/2004 |
| WO | 2014/154188 A1 | 10/2014 |

OTHER PUBLICATIONS

Official Communication issued in International Patent Application No. PCT/EP2018/067786, dated Jan. 17, 2019.
Krejci et al., "Single grating method for low dose 1-D and 2-D phase contrast X-ray imaging", Journal of Instrumentation, Institute of Physics Publishing, vol. 6, No. 1, Jan. 11, 2011, 11 pages.

(Continued)

*Primary Examiner* — Edwin C Gunberg
(74) *Attorney, Agent, or Firm* — Stinson LLP

(57) ABSTRACT

A phase contrast imaging (PCI) method in which, instead of using an analyzer grid, detector pixels are grouped and only a part of the total pixels are used to calculate a phase contrast image. In second, third, etc. steps, the pixels which were not used in the previous recalculation are used additionally to recalculate second, third, etc. phase contrast images. Finally the different phase contrast images are fused to result in a full image.

13 Claims, 14 Drawing Sheets

(56) References Cited

OTHER PUBLICATIONS

Krejci et al., "Hard x-ray phase contrast imaging using single absorption grating and hybrid semiconductor pixel detector", Review of Scientific Instruments, vol. 81, No. 11, Nov. 5, 2010, 5 pages.
Krejci et al., "Semiconductor pixel detector with absorption grid as a tool for charge sharing studies and energy resolution improvement", Journal of Instrumentation, Institute of Physics Publishing, vol. 6, No. 12, Dec. 13, 2011, 11 pages.

* cited by examiner

PHASE CONTRAST IMAGING METHOD

CROSS REFERENCE TO RELATED APPLICATIONS

This application is a 371 National Stage Application of PCT/EP2018/067786, filed Jul. 2, 2018. This application claims the benefit of European Application No. 17181154.0, filed Jul. 13, 2017, which is incorporated by reference herein in its entirety.

BACKGROUND OF THE INVENTION

1. Field of the Invention

The present invention relates to phase contrast imaging (PCI).

2. Description of the Related Art

Phase contrast imaging is an imaging technique that is based on the detection of small variations in the direction of x-ray beamlets obtained e.g. by means of a grating in between an x-ray source and a subject under examination, said variations being detected by means of an assembly of a detector mask placed before an x-ray detector.

PCI is a method that uses other sources of contrast than conventional absorption x-ray imaging. Thus additional information of the composition and structure of biological samples and other samples can be visualized.

Phase contrast imaging in general as well as in this specific invention is not restricted to medical imaging and could also be applied in other application fields such as industrial applications, e.g. non-destructive material testing (NDT) or security applications etc.

Basically two approaches exist:
1. An interferometric approach which uses a partially coherent source of radiation referred to as Talbot-Lau interferometry
2. A completely in-coherent approach with repeated edge illumination referred to as Coded Aperture Phase Contrast Imaging.

Although the present invention is applicable to both techniques, it will be described further on with reference to the Coded Aperture Phase Contrast Imaging technique. The present invention is not limited to this embodiment. The principle of coded aperture phase contrast imaging (PCI) has been described in U.S. Pat. No. 7,869,567.

X-rays emitted from an x-ray source are formed into individual beamlets by means of a sample mask. These beamlets pass through a sample or object and arrive at individual pixels of a detector through a detector mask. The individual x-ray beamlets are arranged to hit the pixel edge of individual rows of pixels or individual columns of pixels or individual pixels. Small deviations in the individual beamlets (change of propagation direction or beam broadening by the sample or object) cause a significant increase or decrease in the signal hitting the exposed area of the pixel resulting in a significant phase contrast or dark field signal.

As will be explained further on in practice an analyzing grating has to be used to achieve an increase or decrease of the pixel value. This poses a first problem of the state of the art method namely that an analyzing grating is to be provided which needs to be adjusted relative to the detector pixels.

Further, as in medical applications for example where usage of a high power x-ray source improves image quality due to short exposure times, state of the art methods typically require low power tubes and thus long exposure times are needed.

Still further, a part of the dose applied to the patient is not used to gather image information if an analyzing grating is used—and thus either the patient must be exposed to higher dose or the number of quanta used for gathering the image is low, which leads to higher quantum noise.

In the state of the art typically large x-ray detectors are conversion type detectors and have a 100% fill factor. Such detectors are not usable for PCI without an analyzer grating.

There is "optical" cross talk between neighboring pixels due to scattering in the conversion layer.

There is no insensitive gap between the pixels which is required for PCI to detect a movement of a beamlet or beam broadening.

Direct conversion type detectors with a gap between pixels are typically only a few lines wide and/or extremely expensive.

The use of an analyzer grating is thus mandatory which leads to three main disadvantages:
1. The pitch of the grating must fit to the pitch of the detector pixels. This limits the usable source size in the x-ray tube (focal spot—see below). The usage of larger grating structures e.g. with the size of integer multiples of the pixel pitch would require mechanical movement of the analyzer grating in addition to the movement of the coded aperture. Moreover this would significantly increase the number of required single exposures (double; triple . . . ).
2. Even for a grating which is adapted to the pixel pitch and the illumination profile produce by the coded aperture 33% of the radiation at the detector is not used (see FIG. 2: taking first and third image is done with 50% of radiation blocked)
3. Adjustment of the analyzer grating to detector is needed. An analyzer absorber must be positioned exactly between two pixels, this is not easy to realize.

Both methods require a so called analyzer grating close to the detector. The main difference of the analyzer gratings for the two methods is the pitch: for the Talbot-Lau approach a pitch in the range of a few µm is required while the coded aperture technique requires gratings with a pitch in the range of 100 µm.

To record a phase contrast image typically the analyzer grating (Talbot-Lau) or the coded aperture must be moved mechanically or any suitable part of the setup must be moved relative to these gratings.

For each mechanical position of the grating (typically ≥3) an x-ray image is recorded. The images are mathematically combined to calculate the phase contrast image, next to the absorption and dark field image.

Prior art documents Krejci F et al.: "Single grating method for low dose 1-D and 2-D phase contrast X-ray imaging", Journal of Instrumentation, Institute of Physics Publishing, Bristol, GB, vol. 6, no. 1, 11 Jan. 2011 as well Krejci F et al.: "Hard x-ray phase contrast imaging using single absorption grating and hybrid semiconductor pixel detector", review of Scientific Instruments, AIP, Melville, N.Y., US, vol. 81, No. 11, 5 Nov. 2010 disclose a method to generate a phase contrast image, an absorption image, or a dark field image.

SUMMARY OF THE INVENTION

It is an object of the present invention to provide a method and system that solves the above-mentioned disadvantages.

The above-mentioned aspects are realized by a method as set out below.

According to the present invention at least one radiation image of an object is generated and recorded by means of a radiation detector such as a direct or in-direct radiography detector. The emitted radiation beam is split up in so-called beamlets by means of a physical beam splitter or beam splitting grating (also called coded aperture) which blocks part of the radiation beam.

More than one image can be generated by shifting the physical grating in the same way as performed in the state of the art.

The x-ray image (or images) are stored and further used for computation of at least one of an absorption image, a phase image and a dark field image.

In the state of the art method an analyzing grating is used to probe the change of the beam profile of the beamlets induced by an object.

In the present invention this analyzing grating is a virtual grid or grating, implemented as a virtual mask laid over the pixel matrix of the recorded pixel values and thereby "blocking" or "ignoring" some pixels so that their values are not used in the computation of the absorption, phase or dark field image while others remain available for use in the computation. By shifting the virtual mask so that pixels that were used in the computation of one of the above-mentioned images become blocked while other sets of (neighboring) pixels become available for computation of one of these images. The virtual grid thus attains the same result as obtained by the moving analyzing grid in the state of the art.

When a beam splitter is used in the light path from light source to detector some detector pixels of the detector are not irradiated. Hence the total pixel resolution of the detector is not used. In order to increase the resolution again, the beam splitter in a specific embodiment is shifted in a direction parallel to the plane of the detector and so that pixels of the pixel matrix which were not irradiated are now available and can be used to calculate a second, third etc. set of absorption, phase images and dark field images by applying the method described higher.

Finally the different absorption images, the different phase images and the different dark field images can be fused respectively.

To get a fused image the different phase (dark field/absorption) images are fit into one another as is illustrated in FIG. 15. If for example 4 single images are recorded and the coded aperture structure is parallel to the columns of the detector the fusion can be done in the following manner:

1. Take column 1 of image 1 and use it as $1^{st}$ column of the fused image.
2. Take column 1 of image 2 and use it as $2^{nd}$ column of the fused image.
3. Take column 1 of image 3 and use it as $3^{rd}$ column of the fused image.
4. Take column 1 of image 4 and use it as $4^{th}$ column of the fused image.
5. Repeat procedure for $2^{nd}$; $3^{rd}$ . . . columns of the 4 images.

It is obvious that other fusion methods which e.g. include a weighting of the respective pixel groups can be applied. Optionally the sub-images can be brightness adjusted to avoid banding in the fused image. The basic idea of fusing is to produce a complete high resolution image by using sub-images which only contain high resolution information from a part of the object by rearranging the pixel information of the single images into a fused image. An important aspect is that the complete sample is imaged and thus that the total of sub-images contain the complete information of the object—allotted to the respective sub-images.

Specific features for preferred embodiments of the invention are set out below.

Further advantages and embodiments of the present invention will become apparent from the following description and drawings.

DETAILED DESCRIPTION OF THE PREFERRED EMBODIMENTS

Figure 1:
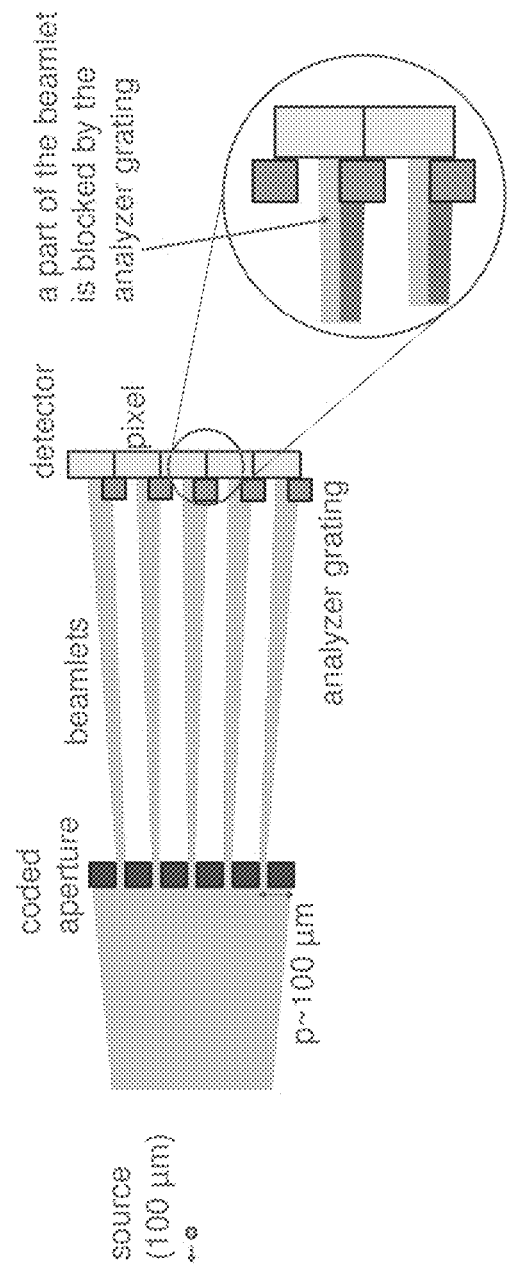
FIG. 1 shows a prior art coded aperture set up.

FIG. 1 shows the typical setup for a prior art coded aperture PCI in which a physical analyzing grating is used.

A source with a small focus is placed at a distance of typically 1 m to 2 m away from the beam splitter grating or coded aperture. The coded aperture has a grid structure that absorbs a part of the x-ray intensity at regular intervals. Behind the grating downstream to the detector the source beam is split into single beamlets. An analyzer grating blocks a part of the beamlets dependent on relative position of the beamlet and the analyzer grating. The pitch of the beamlet structure (x-ray intensity profile) and the analyzer grating are adapted to the pitch of the detector.

When moving the coded aperture (see FIG. 2) the intensity profile is sampled—typically at three points. For these sampling points the phase contrast image can be calculated by applying the following formula [1].

[1] Hard X-ray dark-field imaging with incoherent sample illumination—Marco Endrizzi, Paul C. Diemoz, Thomas P. Millard, J. Louise Jones, Robert D. Speller, Ian K. Robinson, and Alessandro Olivo; Appl. Phys. Lett. 104, 024106 (2014).

$$\begin{cases} t = \frac{2x_1}{\Delta_{MN}} \sqrt{\frac{n}{D+C}} I_2 \exp\left[\frac{1}{2^4} \frac{(D-C)^2}{D+C}\right] \\ \Delta x_R = \frac{x_1}{2} \frac{D-C}{D+C} \\ \sigma_M^2 = \frac{2x_1^2}{D+C} - \sigma_N^2 \end{cases}$$

where $C = -2\ln(I_1/I_2)$ and $D = -2\ln(I_3/I_2)$.

The classical absorption x-ray image is denoted as t; $\Delta x_R$ is the phase image and $\sigma_M$ the dark field image. $I_1 \ldots I_3$ are the pixel intensity corresponding to the 3 images at different positions of the virtual grating. The index N corresponds to the situation without object and $x_1$ is the displacement of the virtual grating. $A_{NM}$ is the resulting amplitude of the system with object (combination of the illumination profile N and the change by the object M).

The state of the art methods are disadvantageous because:
- an analyzer grating is required,
- the analyzer grating needs to be adapted to the detector pixels,
- a high power x-ray source cannot be used and thus long exposure times are required,
- a part of the dose applied to the patient is not used to gather image information, and thus either the patient is exposed to a high dose or the number of quanta used for the image is low which leads to higher quantum noise.

Figure 16:
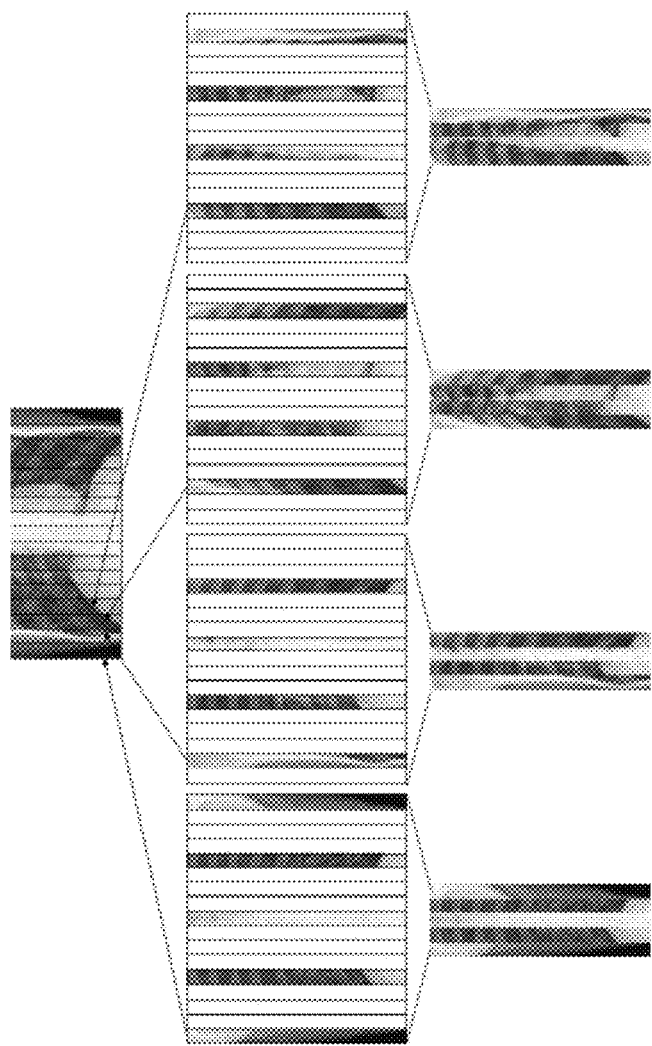
FIG. 16 shows how sub-images are fused to obtain a full PCI image.

According to the present invention, instead of using an analyzer grid the detector pixels are grouped in a special manner and only a part of the total pixels are used to calculate the absorption, phase image and dark field image. The recalculation is done by sequentially using the pixels which were not used in the previous sub-image. In this case the required 3 intensities $I_{1\ldots3}$ can be deduced from a single exposure. In a second, third . . . step the coded aperture is moved to calculate additional phase contrast images as well as absorption and dark field images. Finally the different sub-images are fused (see FIG. 16) to result in full resolution images for phase, absorption and dark field.

The grouping of the pixels to form a virtual grating might be one- or two-dimensional.

Figure 3:
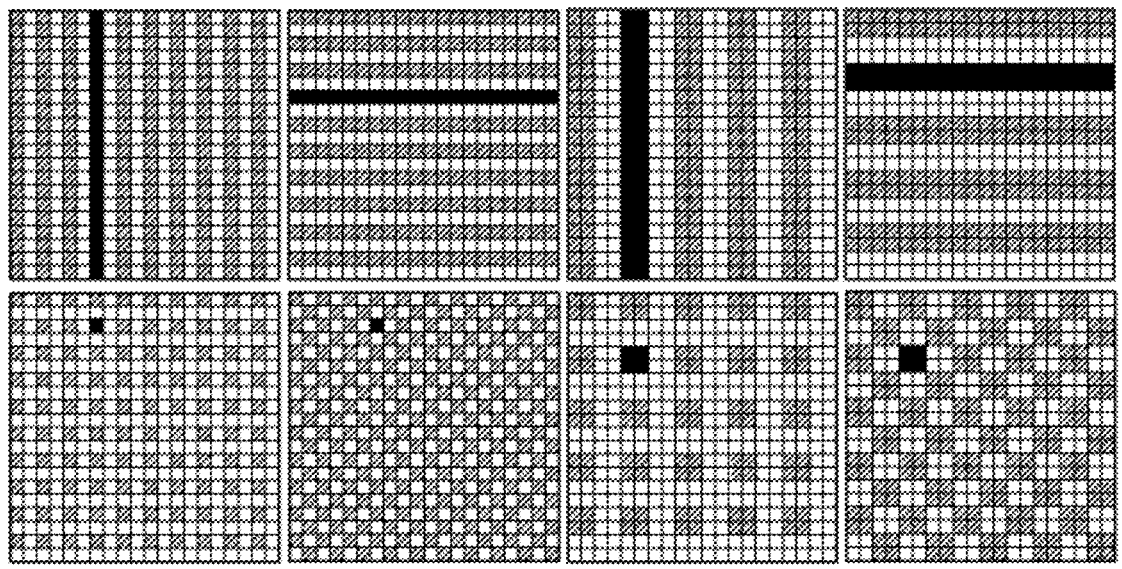
FIG. 3 shows different groupings of detector pixels as used in the context of the present invention.

Different groupings of detector pixels are shown in FIG. 3. (hatched pixels form a group; pixel group sub-structures are marked full black).

The grouping shall not be limited to these examples.

Pixel grouping can be envisaged as if a virtual mask having blocking elements covering pixels that are not used in the calculation of the absorption, phase and dark field images (although the image detector has been exposed and the pixel values are available) and other pixels which are effectively used for the calculation of the absorption, phase and dark field image.

Pixel groups shall preferably have a translation symmetry, i.e. after moving the pixel group by n pixels the pattern shall reproduce (displacement is either in one direction or in two directions; pattern is reproduced either by only moving the groups horizontally OR vertically by n pixels or by moving the pixels horizontally AND vertically by n & m pixels respectively).

The pixel group shall preferably be arranged in a way that the sub-structures do not have direct next neighbors to avoid cross talk.

FIG. 3 shows only line or square substructures but it is also possible to use L-like or open square substructures instead—basically any kind of structure can be used, preferably the structure however fulfills the above requirements.

Figure 4:
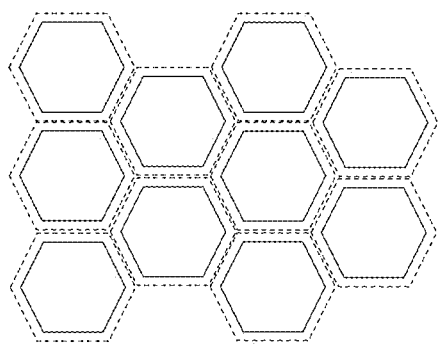
FIG. 4 shows a detector with hexagonal pixels that is particularly suited for diagonal patterning of exposure and detection.

FIG. 4 shows a detector with hexagonal pixels is particularly suited for diagonal patterning of exposure and detection.

The exposure pattern shall be adapted to the group pattern. In the following one-dimensional vertical grouping is used for explanation but it is obvious that this method can also be applied to one-dimensional horizontal or two-dimensional pattern.

A special case of grouping the pixels in a single row (upper left image in FIG. 3) is explained below:

The x-ray intensity pattern exactly fits to the group pattern (in this case it has a pitch of 2 pixels and a 50/50 on-off ratio).

In total 4 images are taken (always the full pixel matrix is stored). For each image the coded aperture is moved by ¼ of the pitch divided by the magnification M of the coded aperture (in this case ½ of a pixel/M). For the first 3 images only the odd [even] columns are used to reconstruct the phase contrast image. The on-off structure of the pixels form a "virtual" analyzer grating. For the reconstruction of the second phase contrast image the coded aperture is moved to the last position (#4) and the images of position #1 and #3 are re-used but now only even [odd] columns are taken into account.

$$M = \frac{Z_{SO} + Z_{OD}}{Z_{SO}}$$

Figure 5:
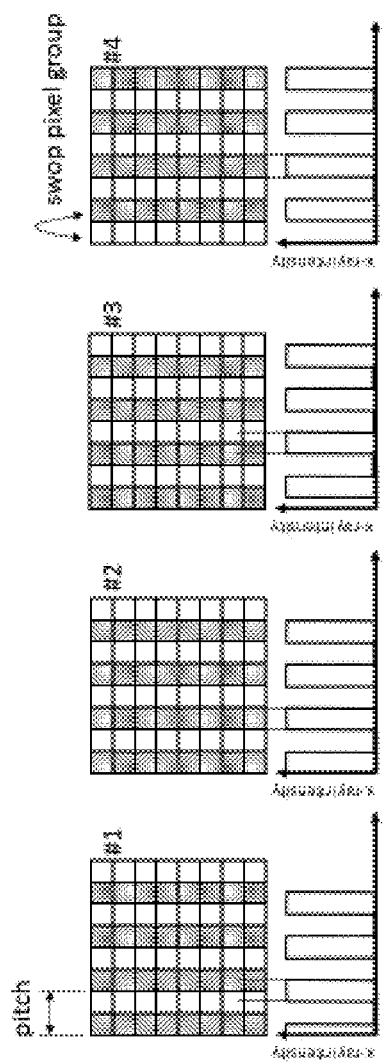
FIG. 5 illustrates an embodiment in which pixels are grouped in a pattern of single horizontal pixel rows. 4 images are taken. For the images taken at grating positions #1 to #3 only the odd [even] columns are used for calculating the phase image. A fourth image is taken with the coded aperture aligned to the even [odd] columns and images #1 and #3 are re-used but now analyzing only the even [odd] columns.

As is shown in FIG. 5, pixels are grouped in a pattern of single horizontal pixel rows. 4 images are taken. For the images taken at grating positions #1 to #3 only the odd [even] columns are used for calculating the phase image. A fourth image is taken with the coded aperture aligned to the even [odd] columns and images #1 and #3 are re-used but now analyzing only the even [odd] columns.

This results in two phase contrast images which can be fused to get the full image.

To improve the quality of the re-calculation of the phase, dark field and absorption image the following procedure is possible: Image "#4 without swopping pixel groups" can be used in addition to #1, #2 and #3. For a non-disturbed signal this would give minimum of the transfer function shown in FIG. 2. The additional information can improve the result.

Analogously, also the second phase contrast image could be reconstructed based on all four images, after swopping pixel groups.

This embodiment is advantageous over the prior art in that by re-using images #1 and #3 for the second reconstruction the x-ray intensity of the ignored pixels during the first reconstruction is NOT lost. When using a real analyzer grating this power would be simply absorbed by the grating and such would be lost. As this happens downstream the patient this would be dose which is "seen" by the patient but not used for image formation when using an analyzer grating.

Figure 6:
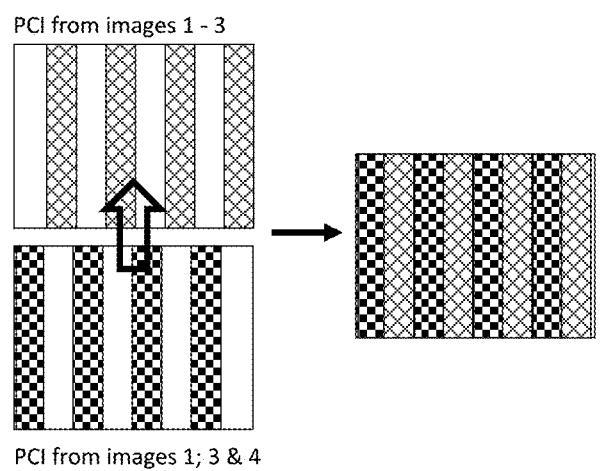
FIG. 6 illustrates phase contrast images calculated from images #1 to #3 and #1; #3& #4 being sorted together to give full information.

FIG. 6 illustrates that phase contrast images calculated from images #1 to #3 and #1; #3& #4 are sorted together to give full information.

Pixel swopping and thus filling the full image by sorting the two images together is only possible with a virtual analyzer grating. Using a real analyzer grating would require to move this grating additionally.

Figure 2:
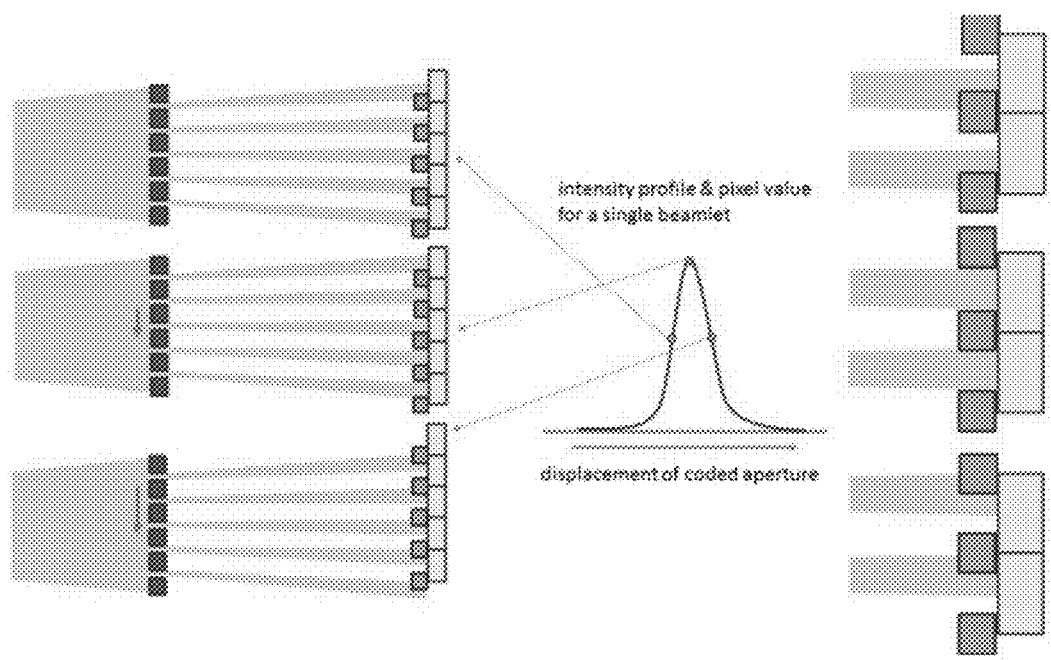
FIG. 2 illustrates a method of capturing a PCI image.

Obviously the pitch of the coded aperture is twice the pitch of the coded aperture as used in a standard setup (compare FIG. 2). This allows not only a simpler production process of the coded aperture grating but also the use of higher power x-ray tubes (see below).

Grouping of Multiple Pixel Rows:

Grouping multiple pixel rows additionally allows a virtual movement of the analyzer grating. This in turn reduces the number or required images.

There are basically three concepts (the following description is for a virtual grating with a pitch of 4 pixels—it is obvious that this method can be extended to the situations with a pitch of 6; 8 . . . pixels):

Use only one position of the coded aperture (no movement)—this will result in reduced resolution and an incomplete transmission (absorption image) as a part of the sample is not illuminated.

Use two positions of the coded aperture (one movement)—this will result in reduced resolution and a complete transmission (absorption image) as the full sample is illuminated.

Use four positions of the coded aperture (three movements)—this will result in full resolution and a complete transmission (absorption image) as the full sample is illuminated.

Figure 7:
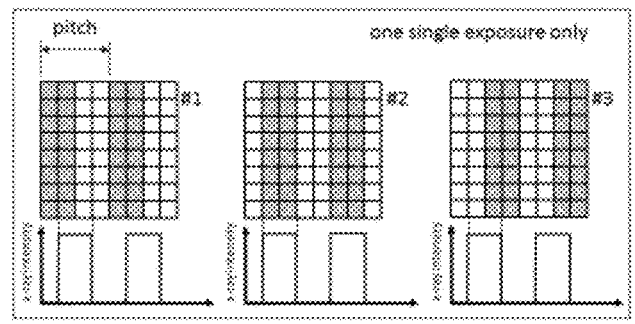
FIG. 7 shows grouping of two vertical columns spaced by two pixels. The coded aperture is not moved. Only one single exposure is performed.

FIG. 7 illustrates the first embodiment.

The coded aperture is fixed and one full image is taken. To calculate the phase contrast image two successive columns are ignored for each of the three required sub-images (only the grouped pixels are used). The three sub-images are computed by shifting the group by one pixel. Obviously there is a part of the sample which is not illuminated.

Figure 8:
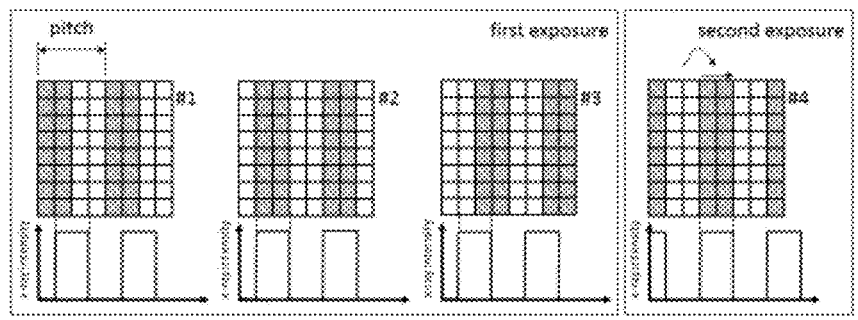
FIG. 8 shows a group of two vertical columns spaced by two pixels. The coded aperture is moved once to get the second image. Two exposures are performed. The selection of the sub-images for the second exposure to re-calculate the phase contrast image is done in a similar way as for the first exposure.

The second embodiment is illustrated in FIG. 8.

In this embodiment the coded aperture is moved by ½ of the pitch divided by the magnification M (in this case 2 pixels/M) for a second exposure. The procedure to get a second phase contrast image is similar to the situation with only one exposure. The two phase images can be sorted together to get a full image—compare FIG. 6. Obviously now the complete sample is illuminated but the resolution is reduced because of the step of the movement of the coded aperture of ½ pitch/M (the maximum resolution would be achieved by moving the aperture by ¼ pitch/M).

Figure 9:
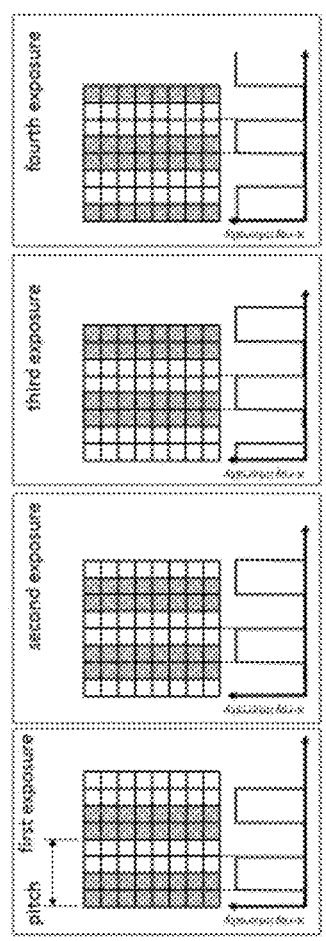
FIG. 9 shows a group of two vertical columns spaced by two pixels. The coded aperture is moved three times to get the second; third & fourth image. Four exposures are done. The selection of the sub-images for the second; third & fourth exposure to re-calculate the phase contrast image is done similarly as for the first exposure.

The third embodiment is shown in FIG. 9.

In this embodiment the coded aperture is moved three times by ¼ of the virtual analyzer grating pitch divided by the magnification M (in this case 1 pixel/M) for a second; third & fourth exposure. The procedure to get a second; third & fourth phase contrast image is similar to the situation with only one exposure. The four phase images can be sorted together to get a full image—compare FIG. 6—now four instead of two sub-images are computed to get one full image.

Of course this can be extended to larger structures of the virtual grating (6; 8 . . . pixel wide structures) and an increased number of sub-images.

To improve the quality of the re-calculation of the phase, dark field and transmission image the following procedure is possible: Use the information of all 4 images at different physical positions of the coded aperture. Use 4 virtual sampling points for each position of the coded aperture. This improves the quality of the result compared to "classical" PCI.

Figure 10:
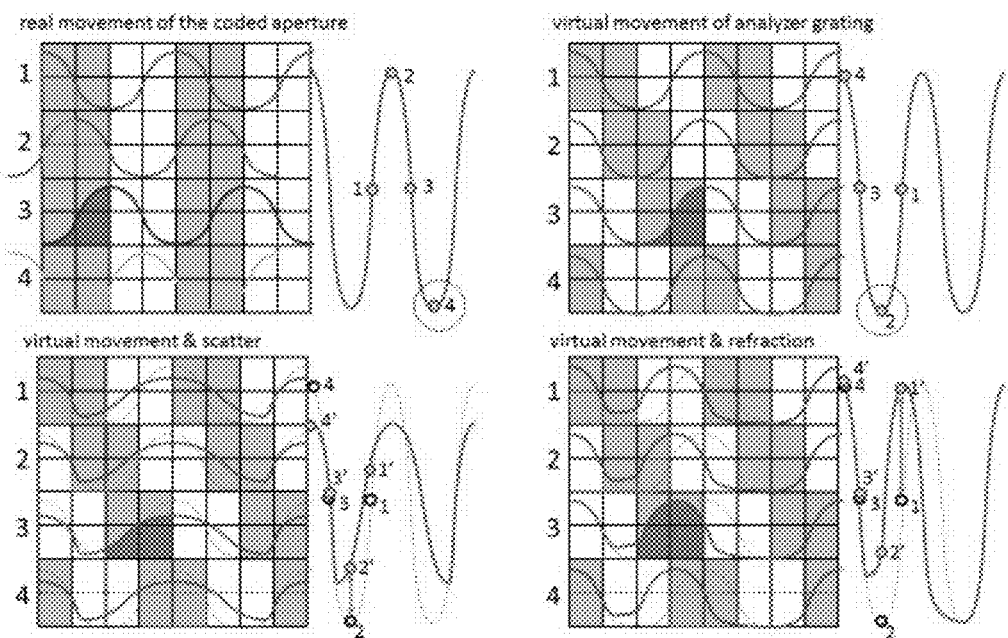
FIG. 10 is an illustration of physical movement and virtual movement.

FIG. 10 is an illustration of physical movement and virtual movement. Compared to "classical" coded aperture PCI additionally a sampling point can be used in the minimum of the undisturbed x-ray profile.

The four sampling points of the real coded aperture & the movement of the virtual analyzer grating offer the advantage that a sampling point in the minimum of the undisturbed x-ray profile can be used (points 2 in FIG. 8a upper right and the two lower images).

Without a sample the signal in the minimum is defined by the penumbra (see below) and the pixel cross talk by scattering in the conversion layer and electron bleeding. This signal can be assumed as a constant offset for a defined set of exposure parameters (tube voltage; tube current; exposure time; filter setting; SID . . . ). The offset can be measured individually for each pixel for a given set of parameters.

With a sample the signal can considerably change (FIG. 10 lower two images) in case of scattering the illumination profile is locally smeared out this causes a large change for the minimum position (FIG. 10: scatter only slightly impacts the other sampling points while the "minimum sampling point" shows a large change). In case of refraction (FIG. 10 bottom, right) there is also a considerable change of the "minimum" sampling point but also of the maximum sampling point.

In general introducing a 4th sampling point will increase the quality of the recalculated phase and dark field image. As this is only connected with a virtual movement of the analyzer grating it is no additional effort to introduce this 4th point. In total 4×4 sampling points are used to reconstruct the complete image.

Obviously again the x-ray power is used more effectively compared to a real analyzer grating which just absorbs. The ignored columns are used to calculate the single phase contrast images. Thus almost all x-ray power passing through the patient is used to generate the image which can reduce the total patient dose considerably—most likely by 30%.

Even though the above explanation is given for a special grouping of the pixels it is obvious that other groupings will give a similar result. E.g. use 3 columns and ignore 3 or use a 2D pattern and perform the procedure in 2D instead of 1D (requires also a movement of the coded aperture in 2D).

Besides the fact that no analyzer grating and thus no adjustment of the grating is required this method also allows to use high power x-ray sources (also called "low brilliance" sources). This can be achieved as the pitch of the virtual grating can be considerably larger than the pitch of the real grating. There is no loss in resolution as the virtual grating can be moved virtually relative to the detector (which typically is not done for a real grating—would require an additional actuator and time) and the coded aperture is moved mechanically (all possible combinations of the real and the virtual positions are used to recalculate the full image).

Figure 11:
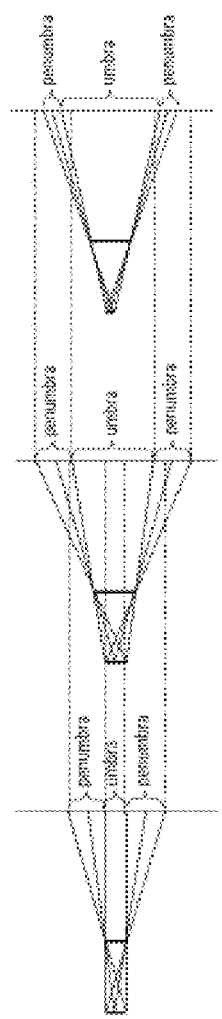
FIG. 11 shows the geometrical construction of umbra and penumbra for different source and object sizes.

The reason why a larger source can be used becomes clear when the umbra and penumbra of an object are considered for different object sizes and different source sizes:

The ratio between umbra and penumbra becomes smaller with increasing source size (FIG. 11 middle and right image) or decreasing object size (FIG. 11 middle and left image).

For a grating the absorbing object is repeated and thus the light intensity of neighboring apertures is superimposed. In case the penumbra is larger than the umbra the modulation depth of the resulting light intensity distribution is very low. The coded aperture only absorbs light without generating a varying intensity profile and thus phase contrast imaging would not be possible.

To get a better estimation of the modulation of the intensity field equations from the following publication can be used:

The relationship between wave and geometrical optics models of coded aperture type x-ray phase contrast imaging systems.

Peter R. T. Munro, Konstantin Ignatyev, Robert D. Speller and Alessandro Olivo, 1 Mar. 2010/Vol. 18, No. 5/OPTICS EXPRESS 4103.

Figure 12:
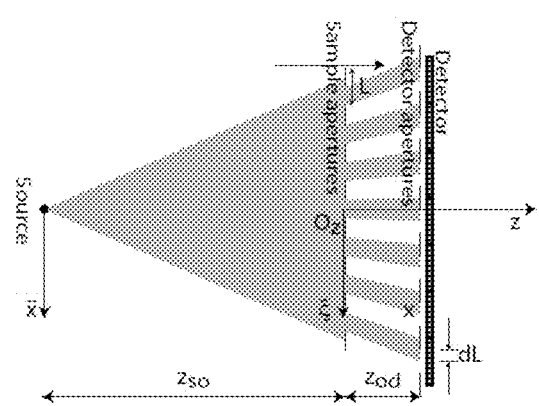
FIG. 12 illustrates an estimation of the intensity distribution after a single pixel.

The estimation of the intensity distribution after a single pixel is illustrated in FIG. 12.

Using the equation of FIG. 12, it is possible to calculate the sensitivity of the system for displacement of the coded aperture. This sensitivity is also important for the re-calculation of the phase contrast image—the higher the better. The approach of coded aperture PCI relies on a change of propagation direction resulting in a local displacement of some beamlets and/or beam broadening of single beamlets—this displacement/broadening must be measured.

Figure 13:
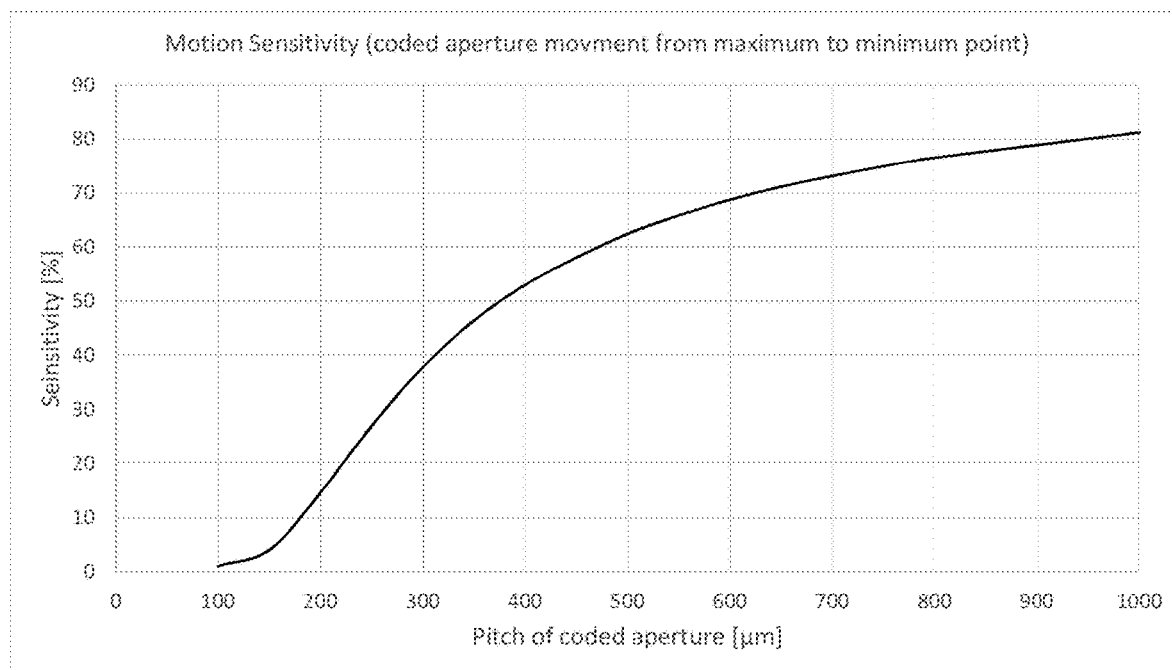
FIG. 13 is a curve illustrating the impact of the pitch of the coded aperture on the system sensitivity; source size 600 µm FWHM (100% reflects a perfect system without penumbra=point source).

The graph shown in FIG. 13 shows an example for typical values of a PCI system (zSO=2 m; zOD=1 m). The source size is chosen to be 600 μm—this is a typical value for the small focus of a standard tube. With such a spot size >20 kW of tube power is possible.

For a detector with a pixel size of 150 μm the classical absorbing analyzer grating pitch must be 100 μm (using the geometry as described above). For a virtual grating with a grouping of two neighboring columns a pitch of 400 μm can be used which increases the sensitivity drastically (53% instead of ~1%).

Furthermore the virtual grating can be rotated versus the coded aperture to generate a Moiré effect. This allows single shot PCI without moving the coded aperture for the cost of resolution.

Figure 14:
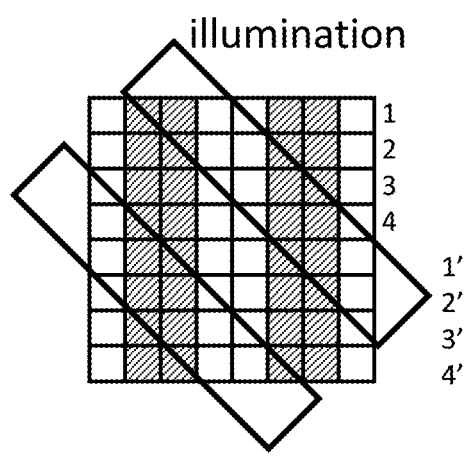
FIG. 14 Illumination (coded aperture) is rotated versus the virtual grating.

FIG. 14 shows an embodiment in which the illumination (coded aperture) is rotated versus the virtual grating.

The angle of rotation is given by the pitch p of the virtual grating in units of pixels and by the number # of required images.

The advantageous of the method of the present invention can be summarized as follows:

No real grating required—lower cost and lower complexity

No adjustment of analyzer grating required—this is a complex process as there are no direct figures which can be used (a microscope will also not help as the pixel boundaries are not visible)

Further advantages are:

Standard low brilliance x-ray sources can be used—this allows short exposure times as tube power can be high (>20 times; comparing the grouping of two columns with the usage of an absorbing analyzer grating).

Figure 15:
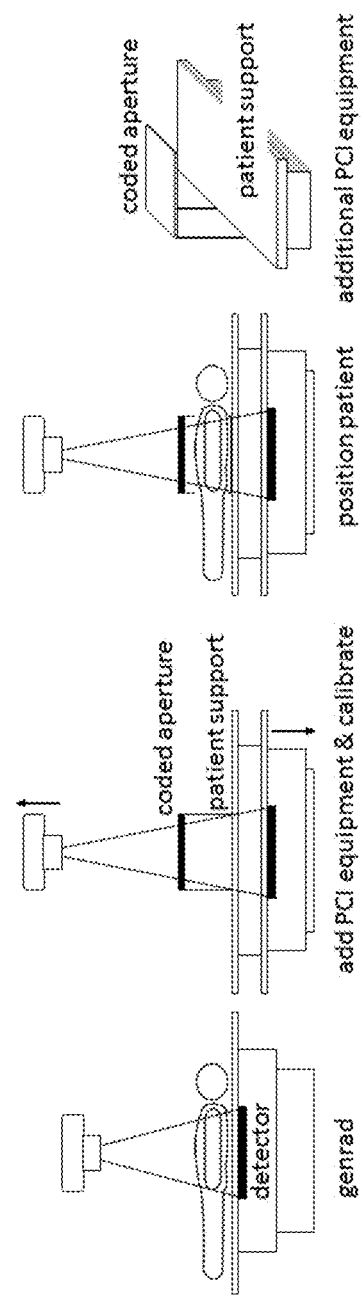
FIG. 15 shows an example how to add on PCI; the coded aperture includes an actuator and logic to calibrate position e.g. using x-ray exposures with out patient.

Due to the lower complexity the additional components for PCI can be removed to allow general radiography exposures or inserted into a standard x-ray system to add PCI capabilities—this is also connected with advantage #3 as a standard tube can be used FIG. 15 is an example of a way to add-on PCI; the coded aperture includes an actuator and logic to calibrate position of the coded aperture e.g. using x-ray exposures without patient.

The invention claimed is:

1. A method for generating at least one of an absorption image, a phase image, or a dark field image of a sample, the method comprising:
   a) applying a beam of radiation emitted by an x-ray source to a beam splitter grating to split the beam into split beams;
   b) introducing the sample into the split beams between the beam splitter grating and an x-ray detector;
   c) measuring a light intensity distribution modulated by the sample with the x-ray detector; and
   d) computing at least one of an absorption image, a phase image, or a dark field image from different sets of pixels detected by the x-ray detector; wherein
   the different sets of pixels are obtained by virtually overlaying a pixel matrix read out from the x-ray detector using a virtual mask including ON/OFF locations and by using the pixels that are covered by the ON locations of the virtual mask to populate a first set of the different sets of pixels, and shifting the virtual mask relative to the pixel matrix to obtain additional sets of the different sets of pixels.

2. The method according to claim 1, wherein a position of the beam splitter grating is fixed, and groups of two pixels of the pixels are envisaged and sub-images are calculated by binning values of the two pixels and shifting the virtual mask by one of the pixels.

3. The method according to claim 1, further comprising:
   moving the beam splitter grating at least once by a given distance parallel to a plane of the x-ray detector and exposing the x-ray detector at each position of the beam splitter grating; wherein
   steps (c) and (d) are repeated at each of the positions of the beam splitter grating so as to obtain a plurality of absorption images, phase images, or dark field images.

4. The method according to claim 3, further comprising:
   generating a full phase contrast image by fusing the absorption images, the phase images, or the dark field images, respectively.

5. The method according to claim 1, wherein sets of the different sets of the pixels have translation symmetry.

6. The method according to claim 5, wherein the virtual mask has a pitch of 4 pixels and the beam splitter grating is stationary; and
   at least one of the absorption image, the phase image, or the dark field image is calculated by shifting the virtual mask 2 times by 1 pixel.

7. The method according to claim 6, further comprising:
   moving the beam splitter grating to two positions spaced apart by a size of two pixels divided by a magnification M of the beam splitter grating; wherein
   absorption sub-images, phase sub-images, or dark field sub-images for each of the two positions of the beam splitter grating are calculated by shifting the virtual mask 2 times by 1 pixel for each position of the beam splitter grating.

8. The method according to claim 7, further comprising:
fusing the absorption sub-images, the phase sub-images, or the dark field sub-images.

9. The method according to claim 6, further comprising:
moving the splitter grating to four positions spaced apart by a size of a pixel divided by a magnification M of the beam splitter grating; and
absorption sub-images, phase sub-images, or dark field sub-images are calculated by shifting the virtual mask 2 times by 1 pixel for each position of the beam splitter grating.

10. The method according to claim 5, wherein the virtual mask has a pitch of 2n pixels, in which n is an integer, and the method further comprises:
moving the beam splitter grating to n positions which are spaced apart by m pixels divided by a magnification M, in which m is an integer and m<n; and
absorption sub-images, phase sub-images, or dark field sub-images are calculated by shifting the virtual mask 2 times by p pixels, in which $1<p<n$ and p is an integer, for each position of the beam splitter grating.

11. The method according to claim 1, wherein the virtual mask has a pitch of 2 pixels and a 50/50 ON/OFF ratio.

12. The method according to claim 11, further comprising:
moving the beam splitter grating to three positions each spaced apart equally; wherein
the image generated with the beam splitter grating in a center position of the three positions corresponds to the ON location of the virtual mask.

13. The method according to claim 11, further comprising:
moving the beam splitter grating to four positions each spaced apart by ¼ of a pixel pitch; wherein
the image generated with the beam splitter in a second position of the four positions corresponds to the ON location of a first virtual mask; and
the virtual mask is swopped so that a fourth position of the four positions of the beam splitter grating corresponds to the ON location of a second virtual mask.

* * * * *